US008204741B2

(12) United States Patent
Hatzianestis et al.

(10) Patent No.: US 8,204,741 B2
(45) Date of Patent: Jun. 19, 2012

(54) MAXIMA SEARCH METHOD FOR SENSED SIGNALS

(75) Inventors: Konstadinos Hatzianestis, Elizabeth Bay (AU); Tony Nygard, Terrigal (AU)

(73) Assignee: Cochlear Limited, Macquarie University, NSW (AU)

(*) Notice: Subject to any disclaimer, the term of this patent is extended or adjusted under 35 U.S.C. 154(b) by 1507 days.

(21) Appl. No.: 10/548,948

(22) PCT Filed: Mar. 29, 2004

(86) PCT No.: PCT/AU2004/000391
§ 371 (c)(1),
(2), (4) Date: May 24, 2006

(87) PCT Pub. No.: WO2004/086217
PCT Pub. Date: Oct. 7, 2004

(65) Prior Publication Data

US 2007/0043555 A1 Feb. 22, 2007

(30) Foreign Application Priority Data

Mar. 28, 2003 (AU) ................................ 2003901538

(51) Int. Cl.
*G10L 11/04* (2006.01)
*A61N 1/08* (2006.01)

(52) U.S. Cl. .......... 704/206; 704/200; 704/207; 607/57; 607/60

(58) Field of Classification Search .................... 607/57, 607/60; 375/245; 341/50; 704/206, 207
See application file for complete search history.

(56) References Cited

U.S. PATENT DOCUMENTS

| | | | | |
|---|---|---|---|---|
| 4,541,275 | A | | 9/1985 | Kerzner |
| 4,745,473 | A | | 5/1988 | Hall |
| 5,313,553 | A | | 5/1994 | Laurent |
| 5,419,331 | A | | 5/1995 | Parker et al. |
| 5,428,999 | A | | 7/1995 | Fink |
| 5,597,380 | A | * | 1/1997 | McDermott et al. ............ 607/57 |
| 6,169,819 | B1 | * | 1/2001 | Dyer et al. .................... 382/232 |
| 6,314,204 | B1 | | 11/2001 | Cham et al. |
| 6,351,568 | B1 | * | 2/2002 | Andrew ........................ 382/239 |
| 6,778,858 | B1 | * | 8/2004 | Peeters ........................... 607/57 |
| 6,909,811 | B1 | * | 6/2005 | Kajiwara et al. .............. 382/246 |
| 7,010,354 | B1 | * | 3/2006 | Grayden et al. ................ 607/57 |

(Continued)

OTHER PUBLICATIONS

Dorman et al. "Performane of spectral maxima and fixed channel algorithms for coding speech in quiet and in noise", Ninth DSP Workshop, Hunt, TX. Oct. 2000.*

*Primary Examiner* — Jialong He
(74) *Attorney, Agent, or Firm* — Kilpatrick, Townsend & Stockton, LLP.

(57) ABSTRACT

An apparatus and method for selecting a set of channels from a plurality channels in a signal processor, the method comprising sampling each one of a plurality of channels and obtaining a binary representation of each one of the samples, arranging each one of the binary representations of samples into a series of bit planes from a most significant bit plane containing the most significant bit of each binary representation, to a least significant bit plane containing the least significant bit of each binary representation, determining those bit planes having binary representations that conform to a predetermined value criteria, and selecting a set of channels by summing bits from each one of those determined bit planes that conform to the predetermined value criteria.

19 Claims, 7 Drawing Sheets

U.S. PATENT DOCUMENTS

2003/0002734 A1* 1/2003 Islam et al. .................... 382/166
2003/0118099 A1* 6/2003 Comer et al. .............. 375/240.2
2003/0135247 A1* 7/2003 Zierhofer ......................... 607/60
2003/0146858 A1* 8/2003 Chen et al. ....................... 341/63
2003/0167077 A1* 9/2003 Blamey et al. .................. 607/57
2003/0171787 A1* 9/2003 Money et al. ................... 607/57
2003/0171934 A1 9/2003 Zhang et al.
2005/0107843 A1* 5/2005 McDermott et al. ............ 607/57

* cited by examiner

BIT PLANE

| CHANNEL NO. | BPL_7 | BPL_6 | BPL_5 | BPL_4 | BPL_3 | BPL_2 | BPL_1 | BPL_0 |
| --- | --- | --- | --- | --- | --- | --- | --- | --- |
| 1 | 0 | 0 | 1 | 0 | 0 | 0 | 1 | 0 |
| 2 | 0 | 0 | 1 | 0 | 0 | 0 | 1 | 0 |
| 3 | 0 | 0 | 1 | 0 | 0 | 1 | 1 | 0 |
| 4 | 1 | 0 | 0 | 0 | 0 | 1 | 1 | 0 |
| 5 | 0 | 0 | 1 | 0 | 0 | 0 | 1 | 0 |
| 6 | 0 | 0 | 1 | 1 | 0 | 0 | 1 | 0 |
| . | | . | | . | | . | | |
| . | | . | | . | | . | | |
| 20 | 1 | 0 | 1 | 0 | 0 | 0 | 1 | 0 |

12

MAXIMA SEARCH METHOD FOR SENSED SIGNALS

CROSS-REFERENCE TO RELATED APPLICATIONS

This application claims the priority of and is a national stage application of PCT Application No. PCT/AU2004/000391, entitled, “Maxima Search Method for Sensed Signals,” filed on Mar. 29, 2004, which claims the priority of Australian Patent No. 2003901538, filed on Mar. 28, 2003. The entire disclosure and contents of the above applications are hereby incorporated by reference.

BACKGROUND

1. Field of the Invention

This invention relates generally to a maxima search method and system for sensed signals, and more particularly, to a maxima search method and system for audio signals processed by a speech processor in cochlea implant systems.

2. Related Art

Audio processors in implantable cochlea implants, and particularly in totally implantable cochlea implants, have extremely tight margins in respect of the amount of power they may consume. For example, the maximum current at standard battery voltage may be as low as 50 microamperes. Commercially available digital signal processors or portable low-power applications manufactured in CMOS technology consume at least one order of magnitude of power more than the aforementioned power restriction.

To provide optimum intelligibility of various parts of the speech spectrum, the selection of M maxima out of the N available analysis channels, when implemented on general purpose signal processors or micro-controllers, requires in the worst case M*N sequential searches over the data set of the N analysis channels. For a typical case of N equal to 20 and M equal to 8, this search scheme would require in the worst case scenario of 160 sequential data comparisons and/or consequently result in long processing delays at a considerable power consumption.

SUMMARY

According to one aspect of the invention there is provided a method for selecting a set of channels from a plurality of channels in a signal processor, the method comprising: sampling each one of a plurality of channels and obtaining a binary representation of each one of the samples; arranging each one of the binary representations of samples into a series of bit planes from a most significant bit plane containing the most significant bit of each binary representation, to a least significant bit plane containing the least significant bit of each binary representation; determining those bit planes having binary representations that conform to a predetermined value criteria; and selecting a set of channels by summing bits from each one of those determined bit planes that conform to the predetermined value criteria.

According to another aspect of the invention there is provided apparatus for selecting a set of channels from a plurality of channels in a signal processor, comprising: a data storage element for each channel for storing a binary representation of a sample in respective channels, wherein each one of the binary representations of samples are arranged into a series of bit planes from a most significant bit plane containing the most significant bit of each binary representation to least significant bit plane containing the least significant bit of each binary representation; whereupon bit planes having binary representations conforming to a predetermined value criteria are determined; and means for summing bits from each one of the determined bit planes that conform to the predetermined value criteria so as to select the set of channels.

According to a further aspect of the invention there is provided a computer program comprising computer program code means for controlling a processing means to execute a procedure to select a set of channels from a plurality of channels in a signal processor, where binary representations of samples in each of the channels are arranged into a series of bit planes from a most significant bit plane containing the most significant bit of each binary representation to a least significant bit plane containing the least significant bit of each binary representation, by: determining those bit planes having binary representations that conform to a predetermined value criteria; and selecting a set of channels by summing bits from each one of the determined bit planes that conform to the predetermined value criteria.

Embodiments of the present invention circumvent the long computational steps of conventional approaches and seeks to exploit data encoding schemes of the analysis channel that encode the energies of the analysis channels which are subsequently stored in hardware thereby minimising the power consumption. Whilst the present invention has obvious adaptation to signal processing for hearing prosthesis, it should be appreciated that this same search method can be equally applied to other applications such as image and radar mapping processes which rely upon searching a selection of sensed signals to identify those signals of interest.

BRIEF DESCRIPTION OF THE DRAWINGS

Preferred embodiments of the invention will hereinafter be described, by way of example only, with reference to the accompanying drawings wherein.

DETAILED DESCRIPTION

A signal processor such as an audio or speech processor in cochlea implants select the M maxima at the output of an analysis filter bank out of the N available analysis channel energies. It uses these M channels in the electrical stimulation of auditory nerves. Depending on the channel analysis method used, this process is repeated every time a new analysis channel or a group of analysis channels is calculated. The method implements custom hardware to handle the selection of channel energies with the greatest magnitudes out of a larger set of available channel energies in a substantially efficient manner with regard to power consumption and the size of a circuit.

Embodiments of the present invention exploit the binary encoding scheme of the values in which the analysis channels' energies are stored. In one example, the value of the energies are encoded as 8-bit binary signals, although a greater or fewer number of binary bits can also be used. An algorithm searches and finds the M channel maxima in eight sequential steps, by searching through one bit-plane at a time. On average the search concludes in less than twelve cycles resulting in a much reduced processing latency and dynamic power consumption as compared to conventional search methods. The algorithm on the bit level finds the M out of the N analysis channels having the largest magnitude. The algorithm operates solely on the data which is stored in a series of registers, one for each channel. In one example, the value of N is variable between 12 and 20 and the value of M varies between 6 and 20.

Figure 1:
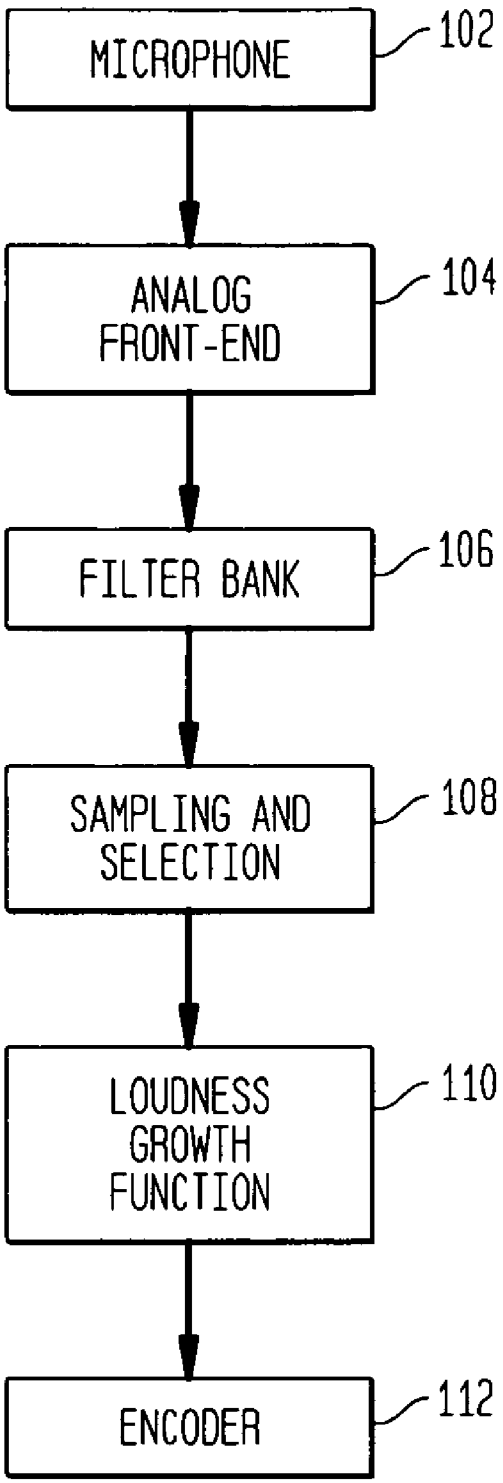
FIG. 1 is a block diagram showing various components of a speech or audio processor.

Shown in FIG. 1 is a schematic block diagram showing the overall signal flow associated with the speech processor according to this particular example. This signal flow defines any one of the following strategies that may be employed in the speech processor, either being SPEAK (Spectral Peak), ACE (Advanced Combinational Encoder) strategy, or CIS (Continuous Interleaved Strategy). Other strategies are envisaged, as will be understood by the person of ordinary skill in the art.

Analogue signals such as speech is detected by a microphone 102 which are then input to an analogue front end 104 to be processed and digitally converted prior to forwarding to a filter bank 106. The filter bank may separate the speech spectrum into a number of frequency channels, typically 20 or 22 channels which are then each sampled at 108. Maxima M are then selected and forwarded to a loudness growth function 110 and from there, to an encoder 112. The resulting signals are then used for processing and analysis by the cochlea implant in order to stimulate the auditory nerves.

Figure 2:
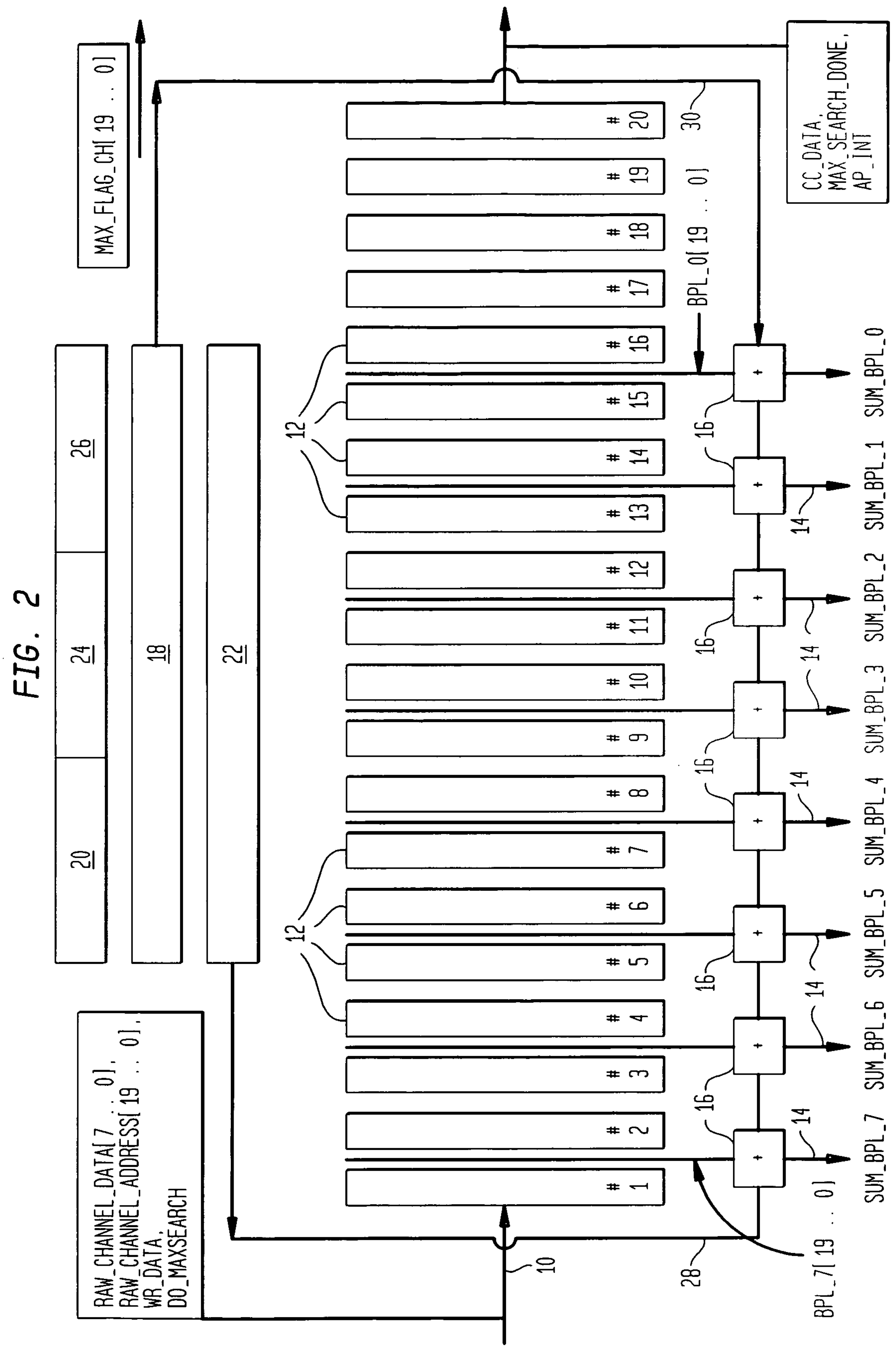
FIG. 2 is a block diagram showing apparatus for selecting maxima values of audio signal channels in an audio processor in accordance with a first embodiment of the invention.

Shown in FIG. 2 is a block diagram of a structure that forms part of the sampling and selection associated with each of the channels derived from the filter bank. It comprises a series of data storage units, in the form of registers with one register per channel, five control registers and eight 5-bit full adders. The structure also employs a state machine to control the maxima searching process. Typically the algorithm or program that initiates and undertakes the maxima searching routines is stored in a separate memory unit such as a PROM.

Data 10 which is input to the bank of registers 12 for each of the 20 channels represent 8-bit samples having a channel address from 19 to 0 to indicate that the sample is to be stored in the appropriately addressed register. Each of the 8-bit samples represents one pass of the envelope spectrum in that particular channel at a particular sampling rate. Thus the original analog signal has been broken down into various channels together with any gain modification, peak detection and base level noise estimation. The sample has then been digitized and forwarded in the data stream 10 to the respective register in the register bank 12. Thus in each of the 8-bit registers 12 there is an 8-bit number for each channel representing the sample.

Each of the bit positions B7 through to B0 represent bit planes (BPL) and each of the values, being either 1 or 0, for each of the channels are fed directly into an adder 16, where there is shown a bank of adders 16, one for each bit plane. Thus for example, the binary values pertaining to each channel in BPL7 are fed directly into adder 16 with the output 14 of the adder 16 being a binary representation of how many channels have a bit that is set or equal to 1 in BPL7. Thus if there are 20 channels, then a 5-bit binary representation is required in case all of the 20 channels have a one in this bit plane.

Figure 3:
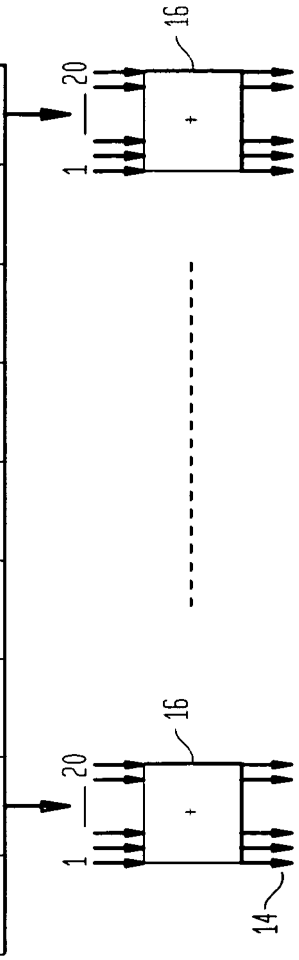
FIG. 3 is a schematic diagram showing bit values in each bit plane of a register bank being forwarded to adder circuits for subsequently indicating maxima or potential maxima values.

Shown in FIG. 3 is an example of 8 bit binary representations of samples for 20 channels in register bank 12. Each of the bit values corresponding to the channels in a particular bit plane, from BPL7 to BPL0, is fed to a respective adder 16 in the bank of adders. For example, the bit values in the most significant bit plane BPL7 are fed to adder 16. The 5-bit representation of the number of binary 1s (or binary zeros) is indicated at the output 14 of the adder 16.

The program or algorithm evaluates the magnitude of the analysis channels iteratively in one bit plane at a time by monitoring the outputs of the 5-bit full adders 16. The program starts with BPL7 and iterates by decrementing the number down to 0 thus arriving eventually at BPL0. It records those channels which are found as maxima in any bit plane, that is signified by a 1 by setting a corresponding flag in a control register 18 identified as Channel Maxima Flag Register (CH_MAX_F_R). Thus for each bit plane there is stored in this register 18 an indication as to which channels are found as maxima. This continues for all of the bit planes where the program monitors the outputs of each of the adders and then arranges to store the maxima found in control register 18. When the number of channels which qualify in any bit plane to be selected as maxima exceeds the target number of maxima M which is stored in the maxima searching register 20, the program records these by setting a corresponding flag in the control register 22 identified as Channel Maxima Flag Intermediate Register (CH_MAX_F_IM_R) which is essentially an intermediate register that flags all channels having potential maxima when the number of set bits in the current bit plane exceeds the target maxima M. These channels will then be used in the next iteration, for example BPL6, if that channel has the value 1 for the particular sample in this bit plane. Where the number of maxima found in the first iteration, with respect to BPL7, such that this number is less than the target maxima M, then the corresponding channels are excluded from the next iteration. This allows other channels, including those having flags set in register 22, to be included to select maxima values therefrom and thereby providing a range of frequencies over which the maxima are selected.

In the iterative search analysis channels in lower bit planes are discarded when maxima have already been found in that channel in higher bit planes. Essentially this means that where a limited number of maxima are to be selected from various channels the highest possible energy values, ideally in BPL7, are selected and then there is no requirement to search for other maxima (bit values of 1) in subsequent less significant bit planes. This assists in reducing the processing time by focussing on channels that as yet have not produced maxima. Furthermore, evaluation of channel magnitudes in lower bit planes is narrowed down only to those analysis channels that are pre-qualified and flagged accordingly in register 22 as mentioned previously. Thus the channels that were stored in register 22 that missed out on selection of definite maxima in previous iterations due to more set bits being found than target maxima could produce maxima depending on the value of the corresponding bit in the channels in the next bit plane.

The above conditions are implemented in hardware as disable and enable variables to each of the 5-bit full adders 14. This is respectively shown by a signal line CH_BPL_ENABLE 28 and a signal line 30 identified as CH_BPL_DISABLE. Thus for those channels where maxima have already been found in an iteration, say for example in BPL7, then for just those channels in lower bit planes the adder is disabled via a signal on line 30. Channels that have been stored as potential maxima in the intermediate register 22 will remain having their adders enabled by signals on line 28 in order to identify further definite maxima as a result of iterations in the lower bit planes.

The maxima search undertaken by the algorithm or program completes the search of the M maxima within eight processing steps or less, depending on the numerical values of the analysis channels. The control register 24 identifies those maxima that have been found in iterations and the control register 26 stores the bit plane number of the various bit planes used in the iteration process.

Figure 4:
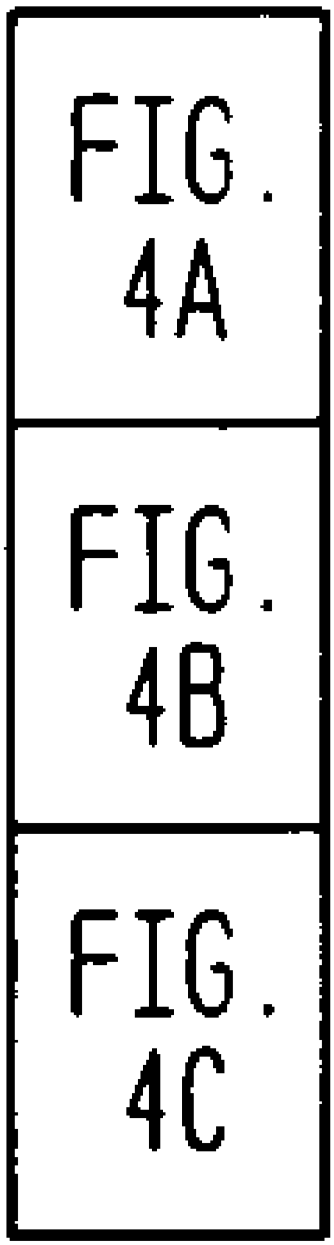
FIG. 4 shows the relationship between the portions of the flowchart illustrated in FIGS. 4A-4C.
Figure 4A:
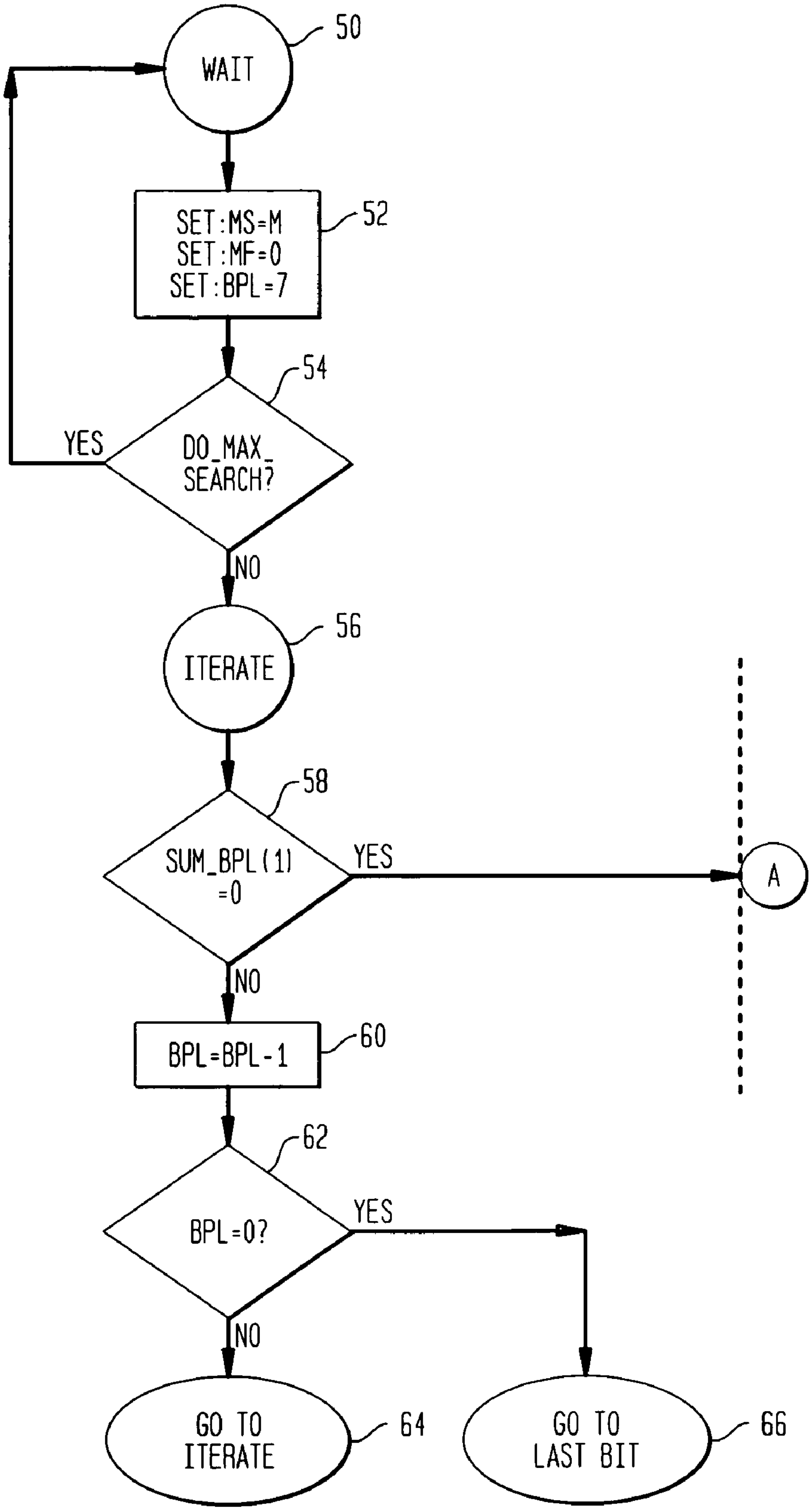
FIGS. 4A-4C are a flow diagram showing the various processes involved in selecting the maximum values.
Figure 4B:
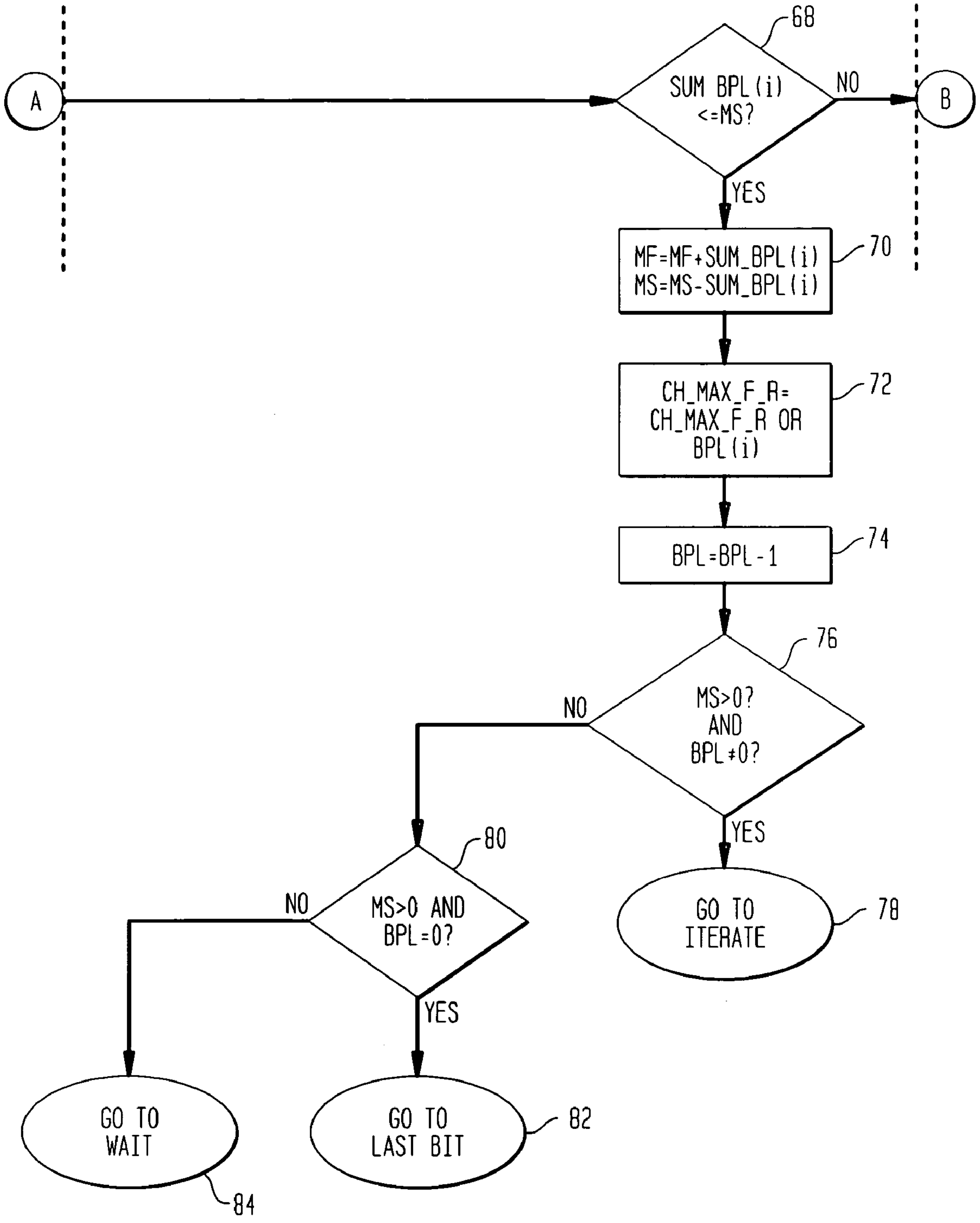
Figure 4C:
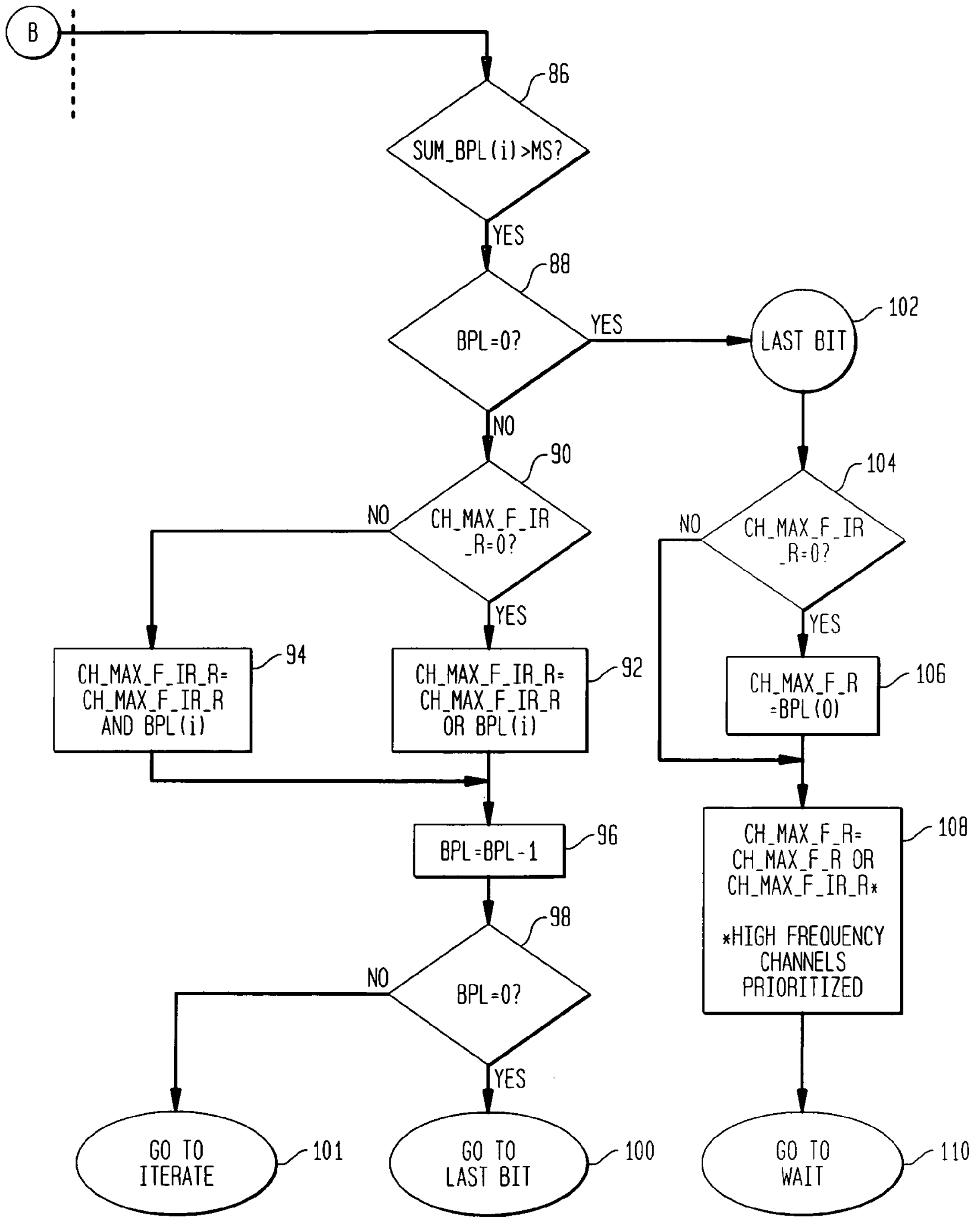

In FIGS. 4A-4C there is shown a flow diagram depicting one exemplary process involved in the maxima search as implemented in the state machine. The particular method used in the search is exact in that it finds M maxima if more than M channels are not zero-valued. It flags the first M channels, high frequencies first, as maxima in the case that more than M channels have the same numerical value. Thus it selects the lower frequencies first to be output as maxima. The maxima search is configurable through firmware with respect to the strategy number of channels N, which typically defaults to 20, and the strategy of maxima M which typically defaults to 6. This process runs at a rate equal to the octave analysis rate of the audio processor and it is started through the channel analysis computational core of the audio processor. The firmware can reprocess data at any time by selecting the appropriate value in an output select register of the audio processor. The converted filter outputs, which can be randomly accessed by the firmware, are zero-valued in the case that they are not part of the current set of channel maxima, or contain the magnitude of the analysis channel as an 8-bit unsigned value when they are part of the current set of maxima.

With respect to FIGS. 4A-4C, the process of the maxima search is started by an executive sequencer in the audio processor which asserts the "DO_MAX_SEARCH" command every time a new analysis channel has been written into an output buffer. Thus the WAIT state 50 indicates that the process is waiting for new analysis channels to be written into the output buffer. In response to the assertion of the start command, the maxima search process starts and initialises its internal registers at step 52. The maxima searching register 20 is set to equal the strategy number of maxima M, that is MS=M. The maxima found register 24 is set to equal 0, that is MF=0 and the initial bit plane index, identified by register 26, is set to the highest bit plane number of the 8-bit implementation, that is BPL=7. Additionally, the intermediate register 22 is set to binary 0 whereby all of the bit positions available for each channel in each bit plane is set to 0. The same occurs for the maxima flag register 18 where all of the bit positions for each channel are set to 0.

At step 54 a determination is made as to whether the maxima search is to be conducted. If not, the process returns to step 50 and if so, an iteration step is initiated at step 56. In the iterate step an evaluation of the number of analysis channels whose magnitude contributes in the current bit plane position is undertaken.

This is accomplished by checking the value "SUM BPL" at the output of the adder circuit in the bank of adders 16 of the current bit plane position. Three cases are possible each time the main state is executed.

If it is found at step 58 that the value of SUM BPL is equal to 0 when no analysis channels contribute a 1 in the current bit plane, the bit plane index BPL is decremented by 1 at step 60 and provided that the next bit plane is not 0 as determined at step 62, the process branches back to the main iterate step 56 at step 64 for the iteration in the next lower bit plane. If the last bit plane has been reached as determined by step 62, then the process goes to the "LAST BIT" 102 at step 66 which is to be described hereinafter.

If at step 58 it is determined that SUM_BPL does not equal 0, then the process moves to step 68 where it is determined whether SUM_BPL is less than or equal to any value stored in the maxima searching register 20, that is M. If this is the case then at step 70 all analysis channels that contribute in the current bit plane will be taken as valid maxima. In this case the maxima sequence increases the value stored in the maxima found register 24 by the value SUM BPL and decrements the value stored in the maxima searching register 20 by the same amount. Essentially this means that additional maxima that are found in the current iteration in the current bit plane are added to the register 24 and the same amount is decremented from the register 20 so that a new number of maxima required is identified.

At step 72 the register 18 which stores the flags of those channels that have been declared as having maxima during the search, is updated by applying a logical OR operation with the bit array variable BPL. This indicates, as an update, which analysis channels in the current bit plane contribute to the maxima search. At step 74 the bit plane index BPL is decremented by 1 and at step 76 a determination is made as to whether the present value of maxima still required in register 20 is greater than 0 and that the bit plane number is not equal to 0. Thus if more maxima are still to be found and the last bit plane has not been reached then the process moves to step 78 and further iterations are undertaken at step 56. If the answer to the process at step 76 is no, the algorithm moves to step 80 where a determination is made as to whether there are still maxima to be found, that is MS is greater than 0 and the last bit plane has been reached. If the last bit plane has been reached then the process goes to the "LAST BIT" 102 at step 82 and if the last bit plane has not been reached and there is still maxima to be found, the process goes back to the WAIT state 50 at step 84.

Returning to the process at step 68, if the SUM BPL is greater than the number of maxima to be found, M identified in register 20, the process moves through step 86 to step 88 where a determination is made as to whether the last bit plane has been reached. If not, the process moves to step 90 where a comparison is made between the value of the register 22 with the decimal 0. This step essentially checks the number of the intermediately flagged channels in the register 22. In the case that it is equal to 0, the process moves to step 92 where the value of the register 22 is updated to the result of the logical OR operation between itself and the bit array variable BPL or the current bit plane. Otherwise, the value of the register 22 is updated to the result of the logical AND operation between itself and the bit array variable BPL at step 94. Essentially the process at step 92 enables channels flagging potential maxima (with bits set) in the present bit plane to be stored in the intermediate register 22 and the process at step 94, where there are already channels flagged as having potential maxima in the intermediate register 22 are AND'ed with the present values in the current bit plane. Thus at step 94 this enables those channels already flagged in register 22 to have the current bit plane values for those channels updated and stored in the register 22. At step 96 the bit plane index BPL is decremented by 1 and then at step 98 a determination is made as to whether the last bit plane has been reached. If that is the case, the process goes to the "LAST BIT" 102 operation at step 100 to be hereinafter described or if the last bit plane has not been reached the process continues iterating at step 101 (back to step 56) to eventually determine maxima based on those channels having nags set in register 22 indicating potential maxima.

Returning to step 88 where the last bit plane has been reached, the final state "LAST BIT" 102 is reached. Here a selection of the remaining channels out of a number of flagged analysis channels, as flagged through the value of the register 22, is undertaken when the last bit plane during the sequential maxima search has been reached. This step ensures that in such situations that multiple analysis channels have equal signal amplitudes, in other words a tie, the channels with the highest frequency allocation are selected as maxima. Thus at step 104 a determination is made as to whether there are any flags set in register 22. If there are no flags set in register 22 the process moves to step 106 where the flags identifying the maxima in register 18 are made equal to corresponding values in the remaining or last bit plane BPL0 and then the process moves to step 108 where the value of the register 18 is updated to the result of the logical OR between itself and the values in the intermediate register 22. The same process occurs for when there are identified at step 104 channels having flags set in the intermediate register 22. After step 108 the process moves to step 110 which indicates that the maxima search is complete and it branches to the initial state WAIT at step 50. Thus essentially this last process from steps 102 to 110 in the event of ties between signal amplitudes of various channels, the process iterates through all of the channels and selects the lowest frequencies as maxima. Alternatively, channels having the highest frequency allocation may be selected as maxima.

Thus where the number of channels flagged in register 22 exceed the number of required maxima that are being searched for, an additional selection step is run after evaluation of the last bit plane is completed. In "LAST BIT" the flags that are set in register 22 are evaluated by starting with the flag position at the channel which has the highest frequency, and then iterating down towards the lower frequency channels. If the flag of the channel under evaluation is set, the register 18 is simply updated to declare the corresponding channel to be a maximum. The iterative step "LAST BIT" repeats until all M maxima are found, or until the last channel with the lowest frequency content has been evaluated by checking the register 22.

As an example of how the flow diagram above is interpreted, consider six analysis channels that are encoded as unsigned magnitudes and where the limit of the maxima required is set to 2. Assuming channel 4 and channel 6 are the current maxima and that the values for the channels are:

Channel 1 equal to 0010 0010
Channel 2 equal to 0010 0010
Channel 3 equal to 0010 0110
Channel 4 equal to 1000 0110
Channel 5 equal to 0010 0010
Channel 6 equal to 0011 0010.

Iterating with the highest bit plane, that is BPL7, the following results:

SUM_BPL7=1
MS=2−1=1
MF=1
CH_MAX_F_R=(000000) BITWISE OR'ed (000100)=000100
CH_MAX_F_IM_R=000000.

Thus, after the iteration in bit plane 7, that is an iteration through the most significant bits of the six channels, it is found that there is one "1" so that one maxima has been found. The program then updates the register 20 by decrementing it by 1 to result in the value 1. Thus one more maxima is required to be found. The register 24 is incremented by 1 and in accordance with step 72 in FIGS. 4A-4C the register 18 is BITWISE OR'ed with the bit values in the current bit plane 7. As the sum of the number of positive bits flagged, being one, is less than MS, the register 22 remains unaffected and does not have any flagged indications indicating channels with excess potential maxima.

By iterating the next bit plane, that is BPL6, the following results:

SUM_BPL6=0
MS=1
MF=1
CH_MAX_F_R=000100
CH_MAX_F_IM_R=000000.

Thus as no bits to the value of 1 were found in bit plane 6, MS and MF remain unchanged as does the value in each of registers 18 and 22.

Iterating through the next bit plane, BPL5, the following results:

SUM_BPL5=5
MS=1
MF=1
CH_MAX_F_R=000100
CH_MAX_F_IM_R=111011.

Thus as the number of potential maxima, identified by bit 1, is equivalent to 5 and therefore greater than the number of maxima required, that is MS=1, these are stored in the intermediate register 22 in the various channel locations. It is noted that as channel 4 has a bit set in the register 18 it has been discarded from the iteration in bit plane 5 and will be for further lower bit planes as a maxima has already been found in channel 4. Thus channels 1, 2, 3, 5 and 6 have bits set in the intermediate register to indicate potential maxima depending on further iterations on further bit planes.

With respect to the next iteration in bit plane 4, BPL4, the following results:

SUM_BPL4=1
MS=1−1=0
MF=1+1=2
CH_MAX_F_R=(000100) BITWISE OR'ed (000001)=000101
CH_MAX_F_IM_R=111011.

Here in the fourth step the search is concluded as all maxima have been found. As the sum of potential maxima in bit plane 4 yielded only one value in channel 6, it is considered a maximum based on having already been set in the intermediate register. Thus the MS is decremented to 0, MF is incremented to 2 and the two maxima originally required have been found. Thus it is equivalent to step 72 wherein the register 18 is BITWISE OR'ed with the current bit plane to yield flags or indications in that register that channels 4 and 6 have maxima found. The register 22 remains unchanged.

It will be appreciated by persons skilled in the art that numerous variations and/or modifications may be made to the invention as shown in the specific embodiments without departing from the spirit or scope of the invention as broadly described.

For example, while the description of the preferred embodiment refers to implementation in hardware and firmware, the method can be implemented entirely in hardware, or entirely in firmware, depending on the specific application. Alternatively, the method can be implemented entirely in software, or, in a combination of software and firmware, or, a combination of software and hardware, or, a combination of software, hardware and firmware.

Moreover, the method can be encoded as a computer program on a computer readable medium, so that the computer program can be subsequently loaded or embedded into a computer system for implementation according to any one of the above arrangements.

The computer readable medium could include a CD-ROM or a floppy disk. Other computer readable medium include magnetic tape, a ROM or integrated circuit, a magneto-optical disk, a radio or infra-red transmission channel, a computer readable card such as a PCMCIA card, and the Internet and Intranets including email transmissions and information recorded on websites and the like. The foregoing are merely exemplary of relevant computer readable mediums. Other computer readable mediums may be practiced without departing from the scope of the invention.

The preferred embodiment has been described with respect to an audio processor for a Cochlear™ implant. However, the method can also be used in signal processor designs for other industries. For example, in the field of ultrasonic imaging the method can be applied in high-speed, real-time processing of reflected ultrasound radiation for measuring tissue impedance. Similarly, in X-ray computed tomography, the method can be used for high-speed, quick-look three-dimensional processing for measuring the intensity of transmitted rays at different angles.

Similarly, the method can be used in laser real-time imaging and laser high-precision ranging.

The method can be used for optical machine vision used for industrial automation applications by means of high-speed optical feature extraction. Microwave and millimeter wave radar applications can benefit from the method in applications such as area surveillance and object tracking by analyzing back-scattered energy in real-time.

In the medical industry, the method can be advantageously applied to various image processing techniques. In the space and defence industries, the method can be used in 2-dimensional real-time signal detection and displays for various sensors (radar, infrared, ultraviolet, sonar etc).

The present embodiments are, therefore, to be considered in all respects as illustrative and not restrictive.

Summary of Certain Aspects and Embodiments

According to a one aspect of the invention there is provided a method for selecting a set of channels from a plurality of channels in a signal processor, said method comprising: sampling each one of a plurality of channels and obtaining a binary representation of each one of the samples; arranging each one of the binary representations of samples into a series of bit planes from a most significant bit plane containing the most significant bit of each binary representation, to a least significant bit plane containing the least significant bit of each binary representation; determining those bit planes having binary representations that conform to a predetermined value criteria; and selecting a set of channels by summing bits from each one of those determined bit planes that conform to the predetermined value criteria.

The predetermined value criteria may comprise maxima values. The method may further comprise the step of identifying each channel having bits of the same sign summed in each bit plane.

The method may further comprise iterating through each bit plane from the most significant bit plane to the least significant bit plane to determine maxima values in each bit plane.

The method may further comprise the step of recording the channels found to have maxima values in any bit plane in a first control register by setting a flag in the first control register.

The method may further comprise setting a limit as to the number of channels having maxima to be selected as output from the signal processor. Preferably the limit of maxima to be found is decremented by the number of maxima found in each iteration of bit planes and the number of maxima found incremented after each iteration of the bit planes.

When the preset limit or decremented limit is exceeded, the method may further comprise the step of recording those channels having potential maxima in a second control register by setting a flag in the second control register for those channels. It may further comprise the step of discarding or discounting maxima values in channels in subsequent bit planes that have already been flagged in the first control register as having maxima values from a higher bit plane, such that those channels are not included in the iteration of the subsequent bit planes.

Where there are channels having maxima flagged in the second control register in a particular bit plane, iterations in subsequent lower bit planes may be limited to such flagged channels in order to find further maxima.

Where the sum of maxima values is taken from any one of the channels in a current bit plane does not exceed the current limit of maxima to be found, any maxima identified in that current bit plane is preferably recorded as valid maxima.

The first control register may be updated after each iteration, with respect to each bit plane searched, by applying a logical OR operation with the current bit plane to indicate the channels in the current bit plane that contribute maxima values.

Where the sum of the total number of bits of the same sign, that is maxima, found in an iteration is greater than the abovementioned limit, the method may further comprise checking intermediately flagged channels in the second control register. If there are no such flagged channels, the value of the second control register is updated to the effect of including the maxima found in the current bit plane. If there are flagged channels in the second control register, the method may further comprise the step of updating the value of the first control register to the effect of including those maxima values of channels already flagged in the second control register.

The method may further comprise the step of selecting maxima from channels having the lowest frequency allocation, which channels have equal signal amplitudes and have been flagged in the second control register, when the least significant bit plane is iterated. Alternatively, the method may comprise the step of selecting maxima from the channels having the highest frequency allocation, which channels have equal signal amplitudes and have been flagged in the second control register, when the least significant bit plane is iterated.

The method may be implemented in a signal processor such as an audio processor in cochlea implant systems, and more particularly in totally implantable cochlea implant systems.

The method may also be implemented in a signal processor such as an image mapping processor or a radar mapping processor.

According to another aspect of the invention there is provided apparatus for selecting a set of channels from a plurality of channels in a signal processor, comprising:

a data storage element for each channel for storing a binary representation of a sample in respective channels, wherein each one of the binary representations of samples are arranged into a series of bit planes from a most significant bit plane containing the most significant bit of each binary representation to least significant bit plane containing the least significant bit of each binary representation;

whereupon bit planes having binary representations conforming to a predetermined value criteria are determined;

the apparatus further comprising means for summing bits from each one of the determined bit planes that conform to the predetermined value criteria so as to select the set of channels.

The predetermined value criteria may comprise maxima values. The summing means may comprise adder logic circuits, one for each bit plane, such that the bit value corresponding to the sample in each channel in a respective bit plane is input to an adder logic circuit and the adder logic circuit preferably adds positive bit values indicative of maxima or potential maxima in each channel.

Preferably each channel is identified when input to the summing means and those channels indicating bits of the same sign are summed in each bit plane. Preferably each bit plane is iterated from most significant bit plane to least significant bit plane in order to determine maxima values in each bit plane.

The apparatus may further comprise a first control register for recording channels found to have maxima values in any bit plane by setting a flag. It may further comprise a maxima searching register for storing a limit as to the number of channels having a maxima that are to be selected to be output from the processor. Preferably the limit of maxima to be found is decremented by the number of maxima found in each iteration of bit planes and the number of maxima found (preferably stored in a maxima found register) incremented cumulatively after each iteration of bit planes. When the limit is exceeded, the apparatus may further comprise a second control register for recording audio channels found to have maxima in excess of the limit by setting a flag in the second control register in those channels. Preferably, maxima values in channels in subsequent bit planes are discarded where those channels have already been flagged as having maxima values in a higher bit plane in the first control register, such that those channels are not included in the iteration of the subsequent bit planes. Where there are channels having maxima flagged in the second control register in a particular bit plane, iterations in subsequent lower bit planes are limited to such flagged channels in order to provide further maxima.

Where the sum of maxima values taken from channels in a current bit plane does not exceed the maxima limit, any maxima identified in the current bit plane is recorded as valid maxima or potential maxima. The number of maxima found is preferably stored in the maxima found register.

The first control register may be updated after each iteration, with respect to each bit plane searched, by applying a logical OR operation with the current bit plane to indicate the channels in the current bit plane that contribute maxima values. Where the sum of the total number of bits of the same sign, or maxima, found in an iteration is greater than the limit, the intermediately flagged channels in the second control register are preferably checked. If there are no channels in the second control register flagged, the value of the second control register may be updated to the effect of including the maxima found in the current bit plane. If there are channels flagged in the second control register, preferably the value of the first control register is updated to the effect of including those maxima values of channels already flagged in the second control register.

Where the least significant bit plane is iterated, preferably the maxima from channels having the highest frequency allocation are selected, which channels have equal signal amplitudes and are also flagged in the second control register.

Preferably the apparatus is applicable to an audio signal processor in cochlea implant systems and more particularly to totally implantable cochlea implant systems. The apparatus may also be applicable to an image mapping processor or a radar mapping processor.

According to a further aspect of the invention there is provided a signal processor having the apparatus according to the second aspect of the invention.

According to a still further aspect of the invention there is provided a computer program comprising computer program code means for controlling a processing means to execute a procedure to select a set of channels from a plurality of channels in a signal processor, where binary representations of samples in each of the channels are arranged into a series of bit planes from a most significant bit plane containing the most significant bit of each binary representation to a least significant bit plane containing the least significant bit of each binary representation, by:

determining those bit planes having binary representations that conform to a predetermined value criteria; and selecting a set of channels by summing bits from each one of the determined bit planes that conform to the predetermined value criteria.

The predetermined value criteria may comprise maxima values. The computer program may further control the processor to iterate through each bit plane from most significant bit plane to least significant bit plane. It may further record in a first control register channels found to have maxima in any bit plane by setting a flag in the first control register. It may further continue such recording in subsequent bit planes until a target number of maxima to be output from the signal processor is reached.

The computer program may control the processor to further record in a second control register channels having potential maxima where the number of channels that qualify in any bit plane to be selected as maxima exceed the target number of maxima to be output from the processor, such recordal being done by setting a flag. It may further discard or discontinue any channels in lower or subsequent bit planes that have maxima flagged in the first control register from iterations in the lower or subsequent bit planes. The evaluation of channels in lower bit planes may be narrowed to those channels having potential maxima flagged in the second control register.

Embodiments of the present invention circumvents the long computational steps of the prior art and seeks to exploit data encoding schemes of the analysis channel that encode the energies of the analysis channels which are subsequently stored in hardware thereby minimising the power consumption. Whilst the present invention has obvious adaptation to signal processing for hearing prosthesis, it should be appreciated that this same search method can be equally applied to other applications such as image and radar mapping processes which rely upon searching a selection of sensed signals to identify those signals of interest.

The invention claimed is:

1. A method for selecting signal channels from a plurality of channels in a speech processor of a hearing prosthesis for processing signals of the selected channels and using the signals of the selected channels to electrically stimulate auditory nerve, comprising:

sampling a plurality of the channels and obtaining a binary representation of a plurality of the samples;

arranging the binary representations of the plurality of samples into a series of bit planes from a most significant bit plane containing the most significant bit of a respective binary representation, to a least significant bit plane containing the least significant bit of a respective binary representation;

determining with a processor which of the series of bit planes include a maxima value; and summing bits, through calculation, of a first determined bit plane corresponding to a determined bit plane that is a most significant bit plane of the series of bit planes including a maxima value;

selecting channels having maxima values in the first determined bit plane when the calculated summation of bits of the first determined bit plane is less than or equal to a predetermined quantity of target channels;

processing respective signals of the selected channels after the channels are selected; and using the signals of the selected channels to electrically stimulate an auditory nerve.

2. The method according to claim 1, further comprising:

identifying each channel having bits of the same sign summed in each bit plane.

3. The method according to claim 1, further comprising:

iterating through each bit plane from the most significant bit plane to the least significant bit plane to determine maxima values in respective bit planes.

4. The method according to claim 3, further comprising:

recording in a first control register the channels found to have maxima values in any bit plan by setting a flag in the first control register.

5. The method according to claim 4, further comprising:

setting a maxima channel limit in a maxima searching register representing the number of channels having maxima values to be selected as output from the signal processor.

6. The method according to claim 5, further comprising:

decrementing the maxima channel limit in the maxima searching register by the number of maxima found in each iteration of bit planes.

7. The method according to claim 5, further comprising:

recording the number of maxima found in a maxima found register and incrementing the number of maxima found in the maxima found register by the number of maxima found in each iteration of bit planes.

8. The method according to claim 7, wherein when the maxima channel limit is exceeded in any iteration of bit planes, the method further comprising:

recording channels having potential maxima in a second control register.

9. The method according to claim 8, further comprising:

discarding maxima values in channels in subsequent bit planes that have maxima values from a higher bit plane flagged in the first control register, such that the discarded channels are not included in an iteration of any subsequent bit plane.

10. The method according to claim 9, wherein the method further comprises:

for channels having maxima flagged in the second control register in a particular bit plane, limiting iterations in subsequent lower bit planes to the channels flagged in the second control register in order to find further maxima.

11. An apparatus for selecting signal channels from a plurality of channels in a speech processor of a hearing prosthesis for processing signals of the selected channels and using the signals of the selected channels to electrically stimulate auditory nerve, comprising:

a data storage device configured to store a binary representation of a plurality of samples of the plurality of channels, wherein the binary representations of the plurality of samples are arranged in the data storage device in a series of bit planes from a most significant bit plane containing the most significant bit of a respective binary representation to a least significant bit plane containing the least significant bit of a respective binary representation; and a processor configured to determine which of the series of bit planes include a maxima value, wherein the apparatus is configured to:

sum bits, through calculation, of a first determined bit plane corresponding to a determined bit plane that is a most significant bit plane of the series of bit planes including a maxima value;

select channels having maxima values in the first determined bit plane when the calculated summation of bits of the first determined bit plane is less than or equal to a predetermined quantity of target channels; and process respective signals of the selected channels after the channels are selected.

12. The apparatus according to claim 11, wherein the apparatus is configured to identify each channel and sum through calculations channels indicating bits of the same sign in each bit plane.

13. The apparatus according to claim 12, wherein the apparatus is configured to iterate through each bit plane from most significant bit plane to least significant bit plane in order to determine maxima values in each bit plane.

14. The apparatus of claim 11, wherein the hearing prosthesis comprises a cochlear implant.

15. A non-transitory computer readable medium comprising:

a computer program code recorded on the non-transitory computer readable medium for controlling a processor to execute a procedure to select signal channels from a plurality of channels in a speech processor of a hearing prosthesis for processing signals of the selected channels and using the signals of the selected channels to electrically stimulate auditory nerve, where binary representations of samples of the channels are arranged into a series of bit planes from a most significant bit plane containing the most significant bit of a respective binary representation to a least significant bit plane containing the least significant bit of a respective binary representation, by:

determining those bit planes including a maxima value;

summing bits, through calculation, of a first determined bit plane corresponding to a determined bit plane that is a most significant bit plane of the series of bit planes including a maxima value;

selecting channels having maxima values in the first determined bit plane when the calculated summation of bits of the first determined bit plane is less than or equal to a predetermined quantity of target channels;

processing respective signals of the selected channels after the channels are selected; and using the signals of the selected channels to electrically stimulate an auditory nerve.

16. The non-transitory computer readable medium according to claim 15 further controlling the processor to iterate through each bit plane from the most significant bit plane to the least significant bit plane.

17. The non-transitory computer readable medium according to claim 16 further recording in a first control register channels found to have maxima in any bit plane by setting a flag in the first control register.

18. The non-transitory computer readable medium according to claim 17 continuing the recording of channels in the first control register found to have maxima in iterations of subsequent bit planes until a target number of maxima to be output from the signal processor is reached.

19. The non-transitory computer readable medium 15, wherein the hearing prosthesis comprises a cochlear implant.

* * * * *